(12) United States Patent
Dragan

(10) Patent No.: US 8,753,613 B2
(45) Date of Patent: Jun. 17, 2014

(54) DENTAL RETRACTION MATERIAL HAVING ENHANCED FLUID ABSORPTION

(75) Inventor: William B. Dragan, Easton, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 12/798,396

(22) Filed: Apr. 2, 2010

(65) Prior Publication Data

US 2010/0255443 A1    Oct. 7, 2010

Related U.S. Application Data

(63) Continuation-in-part of application No. 11/825,802, filed on Jul. 9, 2007, which is a continuation-in-part of application No. PCT/US2007/008232, filed on Mar. 30, 2007.

(60) Provisional application No. 61/212,005, filed on Apr. 6, 2009.

(51) Int. Cl.
*A61K 8/00*    (2006.01)

(52) U.S. Cl.
USPC .............................. 424/49; 424/435

(58) Field of Classification Search
None
See application file for complete search history.

(56) References Cited

U.S. PATENT DOCUMENTS

| | | | |
|---|---|---|---|
| 2,396,203 A | 3/1946 | Robinson | |
| 2,620,502 A | 12/1952 | Russak | |
| 3,056,205 A | 10/1962 | Ennor | |
| 3,238,620 A | 3/1966 | Robertson | |
| 3,380,446 A | 4/1968 | Martin | |
| 3,581,399 A | 6/1971 | Dragan | |
| 3,705,585 A | 12/1972 | Saffro | 128/303.1 |
| 4,071,955 A | 2/1978 | Julius | 32/34 |
| 4,108,979 A * | 8/1978 | Muhler et al. | 424/49 |
| 4,144,882 A | 3/1979 | Takemoto et al. | 128/172.1 |
| 4,173,219 A | 11/1979 | Lentine | 128/260 |
| 4,198,756 A | 4/1980 | Dragan | 222/326 |
| 4,348,178 A | 9/1982 | Kurz | 433/6 |
| 4,396,599 A * | 8/1983 | Sipos | 424/52 |
| 4,468,202 A | 8/1984 | Cohen | 433/199 |
| 4,531,914 A | 7/1985 | Spinello | 433/136 |
| 4,543,063 A | 9/1985 | Cohen | 433/175 |
| 4,551,100 A | 11/1985 | Fischer | 433/218 |
| 4,617,950 A | 10/1986 | Porteous et al. | 132/91 |
| 4,677,139 A | 6/1987 | Feinmann et al. | 523/111 |
| 4,867,680 A | 9/1989 | Hare et al. | 433/37 |
| 4,961,706 A | 10/1990 | Jefferies | 433/39 |
| 5,006,571 A * | 4/1991 | Kumar et al. | 523/120 |
| 5,052,927 A | 10/1991 | Discko, Jr. | 433/90 |
| 5,063,056 A * | 11/1991 | Yamamoto | 424/401 |
| 5,190,457 A | 3/1993 | Schreinemakers | 433/214 |
| 5,213,498 A | 5/1993 | Pelerin | 433/37 |
| 5,266,338 A * | 11/1993 | Cascione et al. | 426/32 |
| 5,362,495 A | 11/1994 | Lesage | 424/435 |
| 5,385,469 A | 1/1995 | Weissman | 433/40 |
| 5,635,162 A | 6/1997 | Fischer | 424/49 |
| 5,639,445 A | 6/1997 | Curtis et al. | 424/49 |
| 5,651,959 A * | 7/1997 | Hill et al. | 424/49 |
| 5,676,543 A | 10/1997 | Dragan | 433/136 |
| 5,795,585 A * | 8/1998 | Ikeda et al. | 424/438 |
| 5,955,513 A | 9/1999 | Hare | 523/109 |
| 5,980,249 A | 11/1999 | Fontenot | 433/80 |
| 6,050,821 A | 4/2000 | Klaassen et al. | 433/214 |
| 6,106,811 A | 8/2000 | Gibbs | 424/52 |
| 6,155,262 A | 12/2000 | Thornton et al. | 128/859 |
| 6,290,941 B1 | 9/2001 | Lahanas et al. | 424/69 |
| 6,375,461 B1 * | 4/2002 | Jensen et al. | 433/136 |
| 6,568,398 B2 | 5/2003 | Cohen | 128/898 |
| 6,616,753 B2 * | 9/2003 | Reddy et al. | 106/718 |
| 6,652,840 B1 | 11/2003 | Prevendar | 424/49 |
| 6,890,177 B2 | 5/2005 | Dragan | 433/136 |
| 7,033,173 B2 | 4/2006 | Coopersmith | 433/136 |
| 7,153,134 B2 | 12/2006 | Coopersmith | 433/136 |
| 7,163,969 B2 | 1/2007 | Ahmed et al. | 523/130 |
| 7,189,075 B2 | 3/2007 | Dragan | 433/136 |
| 7,195,483 B2 | 3/2007 | Dragan | 433/136 |
| 7,241,143 B2 | 7/2007 | Dragan | 433/136 |
| 7,273,623 B2 * | 9/2007 | Kiel et al. | 424/489 |
| 7,328,706 B2 | 2/2008 | Bardach et al. | 128/861 |
| 2003/0228339 A1 | 12/2003 | El-Nokaly et al. | 424/401 |
| 2004/0126740 A1 | 7/2004 | Coopersmith | 433/136 |
| 2004/0180008 A1 * | 9/2004 | Yamaguchi et al. | 424/53 |
| 2004/0234926 A1 | 11/2004 | Halldin et al. | 433/173 |
| 2004/0265777 A1 | 12/2004 | Heasley | 433/136 |
| 2005/0008583 A1 | 1/2005 | White | 424/49 |
| 2005/0069838 A1 | 3/2005 | Kollefrath et al. | 433/136 |
| 2005/0118552 A1 | 6/2005 | Coopersmith | 433/136 |
| 2005/0175959 A1 | 8/2005 | Jodaikin et al. | 433/80 |
| 2005/0202367 A1 | 9/2005 | Kollefrath et al. | 433/136 |
| 2006/0063128 A1 | 3/2006 | Dragan | 433/89 |
| 2007/0065770 A1 | 3/2007 | Lubbers et al. | 433/37 |
| 2007/0218421 A1 | 9/2007 | Narang et al. | 433/136 |
| 2007/0259313 A1 | 11/2007 | Dragan et al. | 433/136 |
| 2007/0264315 A1 | 11/2007 | Fournie et al. | 424/445 |
| 2010/0035213 A1 | 2/2010 | Lubbers et al. | 433/217.1 |
| 2010/0261136 A1 * | 10/2010 | Schulte et al. | 433/88 |

* cited by examiner

FOREIGN PATENT DOCUMENTS

| | | |
|---|---|---|
| GB | 1124976 | 8/1968 |
| JP | 2005179287 A * | 7/2005 |
| WO | WO 2009076332 A2 * | 6/2009 |
| WO | WO 2009/092568 | 7/2009 |

OTHER PUBLICATIONS

JP 2005179287 A (machine translation Jul. 12, 2011).*

*Primary Examiner* — Frederick Krass
*Assistant Examiner* — Dennis J Parad
(74) *Attorney, Agent, or Firm* — Fattibene and Fattibene LLC; Paul A. Fattibene

(57) ABSTRACT

A retraction material promoting both retraction and drying of the gingival sulcus around a tooth. The retraction material comprises an astringent and an absorbing or drying agent. The retraction material is placed with a syringe and capsule around the gingival sulcus prior to the taking of an impression in a dental procedure.

2 Claims, 2 Drawing Sheets

DENTAL RETRACTION MATERIAL HAVING ENHANCED FLUID ABSORPTION

RELATED APPLICATIONS

This application claims the benefit of U.S. Provisional Application No. 61/212,005 filed Apr. 6, 2009.

This application is a continuation-in-part of application Ser. No. 11/825,802 filed Jul. 9, 2007, which is a continuation-in-part of Application No. PCT/US07/008,232 filed Mar. 30, 2007, which are herein incorporated by reference in their entirety.

FIELD OF THE INVENTION

The present invention relates in general to a retraction material used to retract gingiva in dentistry, and more particularly to a retraction material and system facilitating placement of the retraction material around the gingival sulcus.

BACKGROUND OF THE INVENTION

The traditional method for retracting gingival tissue prior to the taking of an impression of a prepared tooth to form a crown or bridge is to mechanically pack a small length of cord saturated with or without an astringent about the base of the tooth to enlarge the gingival sulcus space about the base of a tooth. After a period of time, the cord is removed from the enlarged space defined about the base of the tooth. Upon the removal of the cord, frequently coagulum forms to stop the bleeding or seepage of fluid and is removed with the cord which may result in the seepage of additional bleeding into the space. As a result, an impression cannot be made of the prepared tooth until the additional bleeding can be controlled or stopped. Thus, the traditional procedure for enlarging the space between the gum and the base of the tooth necessary for taking an accurate impression is tedious, time consuming and painful or extremely uncomfortable for the patient. Also, there exists the danger that the dentist may accidentally force the cord beyond the physiologic limit of the space to create a potential periodontal pocket which can cause the tooth to be eventually lost. The general practice of using the cord technique is relatively difficult and tedious for the dentist.

In the event that the space between the tooth and the gum that has to be retracted is very small, it becomes even more difficult for the dentist to place the cord without injuring the gum tissue and from forcing the cord beyond the physiologic limit, and renders the procedure more painful for the patient. Further, the placing of the cord is not a procedure which the dentist may delegate to a dental assistant or dental hygienist. Also, the packing of a retraction cord is a most disliked step to perform during a crown or bridge restoration procedure.

Efforts have been made to obviate the noted disadvantages of affecting the retraction of the gingival tissue by the use of a cord. One such known effort is the use of a kaolin type material that is mixed with an astringent salt which is simply placed about a prepared tooth to absorb the moisture to cause the gum tissue to shrink. Such a product is marketed by Sybron Dental Specialties under the brand name ExpaSyl.

It has been noted that such kaolin type material is packaged in a bulk cartridge similar to a typical anesthetic cartridge commonly used in a dental office that requires the cartridge to be used with a syringe. The end of the cartridge is pierced with a needlelike cannula and the force of the syringing pressure is required to extrude the clay like kaolin material through the cannula. Because of the density of the kaolin type material, the cannula requires the opening to be very large so as to enable the kaolin type material to flow therethrough. The large gauge opening of the cannula renders the bending of the cannula difficult and which bending is often required in order to place the material in difficult to reach places within a patient's mouth. Because the opening of the cannula is quite large, difficulty is encountered in placing the kaolin type material about the gingival sulcus in a manner similar to the traditional method of packing cord to retract the gum tissue.

Also, the use of such kaolin type material to retract the gum tissue tends to crumble, rendering it difficult to place in the space between the gum tissue and the tooth to attain the desired retraction of the gum tissue. Another noted problem with such kaolin type material is the removal of the kaolin material after the period of time required to affect the hemostasis and the retraction. Generally, the kaolin material is required to be washed out using a water-air spray with extreme care to remove all the kaolin material without restarting any bleeding in the gingival sulcus. Another kaolin based material intended to overcome some of these problems is manufactured by Primier Dental Products Company under the trademark Traxodent. This material is packaged in a bulk syringe and is less viscous than other materials, such as ExpaSyl material sold by Sybron Dental Specialties.

Another known technique for effecting a non-cord retraction and/or hemostasis is disclosed in U.S. Pat. No. 5,676,543 issuing to Dragan on Oct. 14, 1997. Therein disclosed is a generally two part process utilizing two different viscosities of a silicone material to effect the cordless retraction and/or hemostasis of the gingival sulcus.

Another retraction device is disclosed in U.S. Pat. No. 6,890,177 issuing to Dragan on May 10, 2005. Therein discloses is a more simplified cordless retraction method and device whereby the cordless retraction may be accomplished by resorting to a porous sponge or foam cellular dam which is shaped to conform with the prepared tooth or teeth, arranged to contain a two part silicone type impression material that includes a base portion and a catalyst, whereby the patient's biting force is utilized to apply the necessary pressure to effect the desired retraction.

Other devices and methods are used to retract the gingival sulcus e.g. Magic foam cord which is dependent upon an expanding silicone material which is a two-part, chemically cured component system that are required to be mixed by the dentist at chair side prior to application and which cures or sets to effect the retraction of the gingival tissue.

Another retraction device is disclosed in U.S. Pat. No. 7,241,143 issuing to Diskco, Jr. et al on Jul. 10, 2007. Therein disclosed is a preloaded tooth dam filled with a non-setting retraction material.

While there have been numerous efforts to improve the difficult procedure of retracting the gingival, many of these efforts have been solely directed to retraction of the gingival. Many of these efforts have resulted in adequate retraction, but have also left blood and saliva resulted in moist or damp margin at the sulcus that resulted in additional time or steps needed for dry the sulcus in order to obtain a good impression. Therefore, there is a need to improve the retraction procedure and to provide a procedure that will result in improved tooth margin areas that will result in the taking of better impressions.

This invention is directed to an improvement to the non-cord retraction devices and procedures described hereinabove for effecting cordless retraction of the gingival tissue by utilizing an improved retraction material that provided better margin or sulcus areas for taking an impression.

SUMMARY OF THE INVENTION

The present invention provides a retraction material achieving both retraction and absorption. The retraction material of the present invention comprises an astringent and absorbing agent. Additionally, a thickening agent may be used to improve placement of the retraction material.

Accordingly, it is an object of the present invention to improve margin or sulcus area resulting in the taking of better impressions.

It is another object of the present invention to make retraction and impression preparation easy and efficient.

It is an advantage of the present invention that retraction and drying of the sulcus is accomplished in a single step.

It is another advantage of the present invention that the retraction martial is easily applied.

It is a feature of the present invention that an astringent and an absorbing agent are provided in a single retraction material.

It is another feature of the present invention that it is applied precisely with a syringe.

It is yet another feature of the present invention that the retraction material may be applied with cannulae that may be easily bent.

It is still another feature of the present invention that the retraction material may be dispensed with a plastic capsule or tip having a nozzle.

It is yet another feature of the present invention that a gentle water spray may be used that does not disturb the blood coagulum.

These and other objects, advantages, and features will become more readily apparent in view of the following detailed description.

DETAILED DESCRIPTION OF THE PREFERRED EMBODIMENTS

Figure 1:
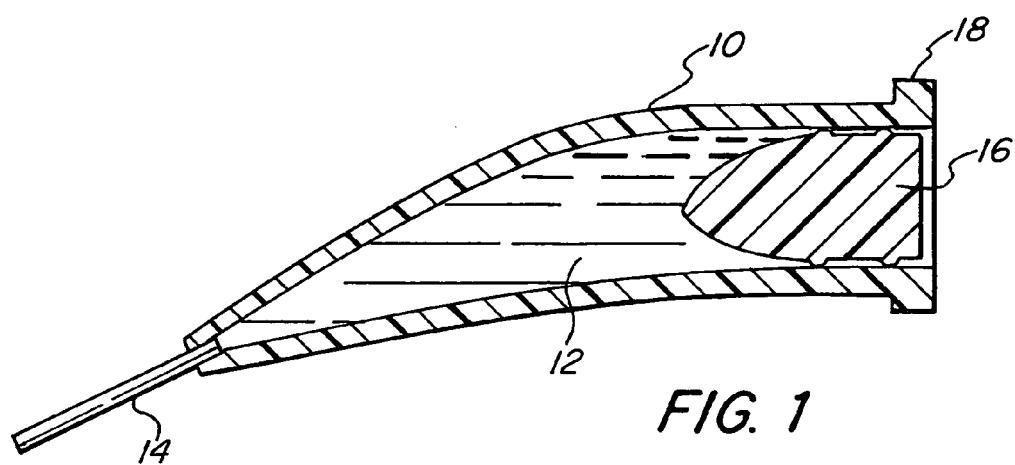
FIG. 1 schematically illustrates the present invention and the retraction material in a dispensing capsule.

FIG. 1 schematically illustrates the present invention and retraction material of the present invention in a capsule 10. The capsule 10 aids in dispensing and placement of the retraction material 12 placed in the capsule 10. At the discharge end of the capsule 10 there may be placed a needle cannula 14, and at the other or loading end of the capsule 10 is a plug or piston 16. The plug or piston 16 is advanced toward the dispensing end to extrude the retraction material 12. A flange 18 is placed at the loading end to attach to a syringe or other device to displace the plug or piston 16. Preferable the syringe or other device has a mechanical advantage such as the manual extruder disclosed in U.S. Pat. No. 4,198,756 issuing to Dragan on Apr. 22, 1980, which is herein incorporated by reference. The syringe may also be of the type disclosed in U.S. Pat. No. 3,581,399 issuing to Dragan on Jun. 1, 1971, which is herein incorporated by reference.

Figure 2:
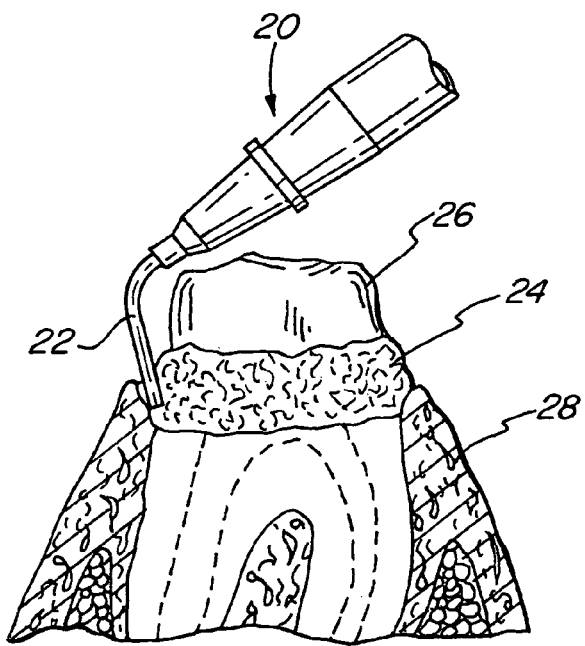
FIG. 2 schematically illustrates application of the present invention and dispensing of the retraction material around a prepared tooth.

FIG. 2 illustrates the technique of applying the retraction material 24 around a prepared tooth 26. A dispensing system or capsule and syringe combination 20 with a needle cannula 22 is used to dispense the retraction material 24 around the prepared tooth 26 within the gingival sulcus of the gingiva or gum 28. The retraction material is used to retract the gingiva so that a good impression of the prepared tooth may be made in a dental procedure to cap or restore the prepared tooth 26.

The retraction material of the present invention has the unique properties of both providing retraction and absorption. The absorption or drying property aids in drying the gingival sulcus between the tooth and gingiva or gum aiding in removing excess fluids or blood which interfere with the taking of a good impression of the tooth and surrounding area. The impression is used in the dental procedure to restore the tooth. The impression of the tooth area may be done with conventional silicone based impression material or by digital imaging methods.

The retraction material comprises an astringent, absorbing agent, and a thickener. The astringent may be any material having astringing properties, such as aluminum chloride, aluminum sulfate, ferric chloride, sodium chloride, aluminum potassium sulfate, ammonium aluminum sulfate, tannic acid and any other equivalent or known astringent material. The absorbing or drying agent may be any material having absorbing or drying properties, such as potassium polyacrylate, sodium polyacrylate, sodium sulfate, silica gel, magnesium sulfate, calcium sulfate, corn starch, calcium chloride, sodium chloride, and any other equivalent or known absorbing or drying material or chemical desiccant. The thickening agent may be any material having thickening properties, such as corn starch, guar gum, xanthan, fumed silica, and any other equivalent or known thickening material.

A preferred formulation of the retraction material of the present invention is indicated below.

| Amount | Material | Comments |
| --- | --- | --- |
| 100 cc of 5% to 40% solution In distilled water | Aluminum chloride hexahydrate | |
| 2 to 30 grams | Sodium polyacrylate | Added to solution through sieve, particle size ranging from between 0.0100 mm to 0.00001 mm, and preferably between 0.0077 mm and 0.00010 mm |
| 5 to 50 grams | Fumed silica | Added to solution through sieve |

Several formulations of the retraction material have been prepared and in testing have been successful in aiding retraction. The different formulations are indicated below.

Formula 1

A 25% saturated solution of aluminum chloride was prepared in 50 cc of distilled water. To the aluminum chloride solution 5 grams of sodium polyacraylate and 10 grams of fumed silica was added through a sieve.

Formula 2

A 25% saturated solution of aluminum chloride was prepared in 100 cc of distilled water. To the aluminum chloride solution 10 grams of sodium polyacraylate and 20 grams of fumed silica was added through a sieve.

Formula 3

A 25% saturated solution of aluminum sulfate was prepared in 50 cc of distilled water. To the aluminum sulfate solution 5 grams of sodium polyacraylate and 10 grams of fumed silica were added through a sieve.

Formula 4

A 100% saturated solution of sodium chloride was prepared in 50 cc of distilled water. To the sodium chloride solution 5 grams of sodium polyacraylate and 4 grams of fumed silica were added through a sieve.

Formula 5

A 100% saturated solution of sodium chloride was prepared in 50 cc of distilled water. To the sodium chloride solution 10 grams of sodium polyacraylate was added through a sieve.

The following Formula 6 has been prepared and found to be particularly preferred and beneficial in performing retraction of gingiva due to its ease of delivery and retraction affect.

| Formula 6 | | | |
| --- | --- | --- | --- |
| Amount (grams) | Material | Preferred Percent by Weight | Percent Range by Weight |
| 500 | Distilled Water | 56.5% | 50%-60% |
| 125 | Aluminum Chloride | 14.1% | 10%-20% |
| 90 | Sodium Polyacraylate | 10.2% | 5%-15% |
| 170 | Fumed Silica | 19.2% | 15%-25% |

Other water soluble carries, such as glycerin may also be used in this formula. Therefore, water, glycerin or any water soluble agent may be a carrying agent for the ingredients in the different formulations.

The main purpose of these formulas is to create a heavy gel or paste that can be easily inserted directly into and around the gingival sulcus through a very small opening either through a cannula or a small discharge nozzle of a capsule, such as the capsule disclosed in U.S. Pat. No. 3,581,399 issuing to Dragan on Jun. 1, 1971, which is herein incorporated by reference.

The retraction material of the present invention has a heavy gel type or paste like consistency making it ideally suited to dispensing with a capsule or tube having a needle cannula or small diameter discharge nozzle. The retraction material can be extruded or dispensed through a needle cannula as small as from 18 to 22 gauge. This greatly facilitates precise and easy placement of the retraction material directly into the gingival sulcus. Additionally, injecting the gel has a mechanical action to help retract the gingival sulcus. The capsule or tube may have a needle cannula or may be any capsule or tube, and is preferably a capsule and cannula similar to the one disclosed in U.S. Pat. No. 5,052,927 issuing to Discko, Jr. on Oct. 1, 1991, which is herein incorporated by reference. Another capsule or tube without a needle cannula that may be used is disclosed in U.S. Pat. No. 3,581,399 issuing to Dragan on Jun. 1, 1971, which is herein incorporated by reference.

Figure 3:
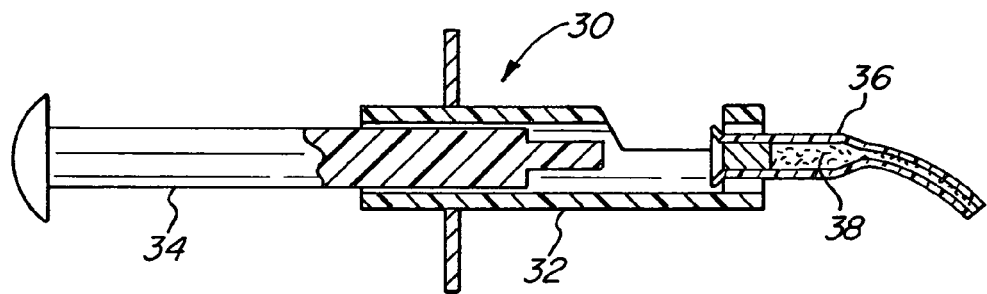
FIG. 3 is an elevational view illustrating a syringe used to dispense the retraction material.

FIG. 3 illustrates a delivery system with a capsule or tube suitable of delivering the retraction material of the present invention. A syringe 30 has a barrel 32 and a reciprocating plunger 34 placed within the barrel 32. A capsule or tip 36 is held within the barrel 32. The capsule or tip 36 may be made of plastic and has a long curved nozzle for precisely placing the retraction material 38 contained therein.

Figure 4:
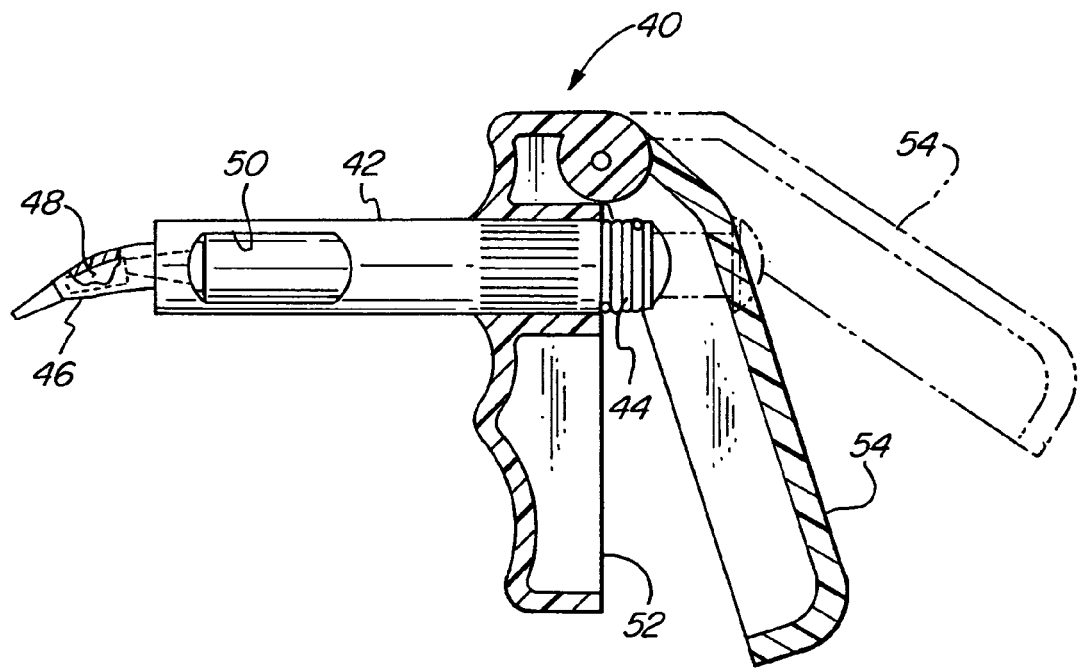
FIG. 4 is an elevational view illustrating a syringe having a mechanical advantage or lever used to dispense the retraction material.

FIG. 4 illustrates another delivery system having a mechanical advantage or lever with a capsule or tube suitable for delivering the retraction material of the present invention. A syringe 40 has a barrel 42 and a reciprocating plunger 44 placed within the barrel 32. A capsule or tip 46 may be made of plastic and has a long curved nozzle for precisely placing the retraction material 48 contained therein. The capsule or tip 46 is placed in the barrel 42 through breach opening 50. A stationary handle 52 is placed on the barrel 42 and a movable handle 54 is used to advance the plunger 44.

The retraction material of the present invention can be used in a dental procedure for restoring a tooth according to the following method steps.

1. Preparing a tooth or teeth for a restoration;
2. Placing the retraction material in a capsule with or without a needle cannula and placing the capsule in a syringe;
3. If the capsule has a needle cannula, bending the needle cannula to provide easy access to the gingival;
4. Placing the needle cannula or tip of the capsule into the gingival sulcus and slowly injecting the retraction material around the gingival sulcus and the entire perimeter or circumference of the tooth or teeth;
5. Letting the retraction material remain or stand for between 2 and 5 minutes depending upon the amount of gingival crevicular fluid;
6. Gently rinsing the retraction material away;
7. Drying the area around the tooth or teeth; and
8. Proceeding with dental procedure, such as taking an impression.

The additional step of adding pressure with a cap placed over the tooth or teeth and gingival sulcus may also be practiced, preferably between steps 4 and 5 above. The biting pressure of the patient holding the material in close proximity will aid in the retraction of the gingival sulcus.

While the present invention has been described with respect to several embodiments, it will be understood that various modifications may be made without departing from the spirit or scope of the invention.

What is claimed is:

1. A retraction material comprising a gel or paste, for use in a dental procedure for retracting gingival tissue from around a tooth and widening a gingival sulcus, comprising:
    a) 10 to 20 percent by weight of an astringent selected from the group consisting of aluminum chloride, aluminum sulfate, ferric chloride, sodium chloride, aluminum potassium sulfate, ammonium aluminum sulfate, and tannic acid;
    b) 5 to 15 percent by weight of an absorbing agent selected from the group consisting of potassium polyacrylate, sodium polyacrylate, sodium sulfate, silica gel, magnesium sulfate, calcium sulfate, calcium chloride and kaolin; and
    c) 15 to 20 percent by weight of a thickening agent selected from the group consisting of corn starch, guar gum, xanthan, and fumed silica;
    wherein said retraction material
        i) can be extruded or dispensed through a cannula;
        ii) permits retraction and drying of the sulcus in a single step; and
        iii) can be rinsed away after retraction with a gentle water spray without disturbing blood coagulum.
2. The retraction material of claim 1, wherein the cannula is an 18 to 22 gauge cannula.

* * * * *